United States Patent
Sparbier et al.

(10) Patent No.: US 10,480,020 B2
(45) Date of Patent: Nov. 19, 2019

(54) RAPID TEST FOR MICROBIAL RESISTANCES BY MASS SPECTROMETRY

(71) Applicant: Bruker Daltonik GmbH, Bremen (DE)

(72) Inventors: Katrin Sparbier, Bremen (DE); Beatrix Wegemann, Bremen (DE)

( * ) Notice: Subject to any disclaimer, the term of this patent is extended or adjusted under 35 U.S.C. 154(b) by 261 days.

(21) Appl. No.: 15/089,653

(22) Filed: Apr. 4, 2016

(65) Prior Publication Data

US 2016/0298164 A1    Oct. 13, 2016

(30) Foreign Application Priority Data

Apr. 13, 2015    (EP) .................................... 15163322

(51) Int. Cl.
*C12Q 1/18*    (2006.01)
*H01J 49/04*   (2006.01)

(52) U.S. Cl.
CPC ............ *C12Q 1/18* (2013.01); *H01J 49/0418* (2013.01)

(58) Field of Classification Search
None
See application file for complete search history.

(56) References Cited

U.S. PATENT DOCUMENTS

| | | |
|---|---|---|
| 2014/0306104 A1 | 10/2014 | Futterer et al. |
| 2014/0335556 A1 | 11/2014 | Franzen et al. |

FOREIGN PATENT DOCUMENTS

| | | |
|---|---|---|
| EP | 2801825 A1 | 11/2014 |
| EP | 2806275 A1 | 11/2014 |
| WO | 2009065580 A1 | 5/2009 |
| WO | 2011154517 A1 | 12/2011 |
| WO | 2012023845 A1 | 2/2012 |
| WO | 2014187517 A1 | 11/2014 |

OTHER PUBLICATIONS

Bruker "Bruker Guide to MALDI Sample Preparation" Sep. 2012, 19 pgs (Year: 2012).*
Jorgensen et al. "Antimicrobial Susceptibility Testing: A Review of General Principles and Contemporary Practices" Clinical Infectious Diseases 2009; 49:1749-55 (Year: 2009).*
Reinecke, K.: Massenspektrometrie-basierte Hochdurchsatz-Protein-Liganden-Bindungsassays, dissertation, Jan. 1, 2006 (Jan. 1, 2006), pp. 1-213, Located on the Internet: URL: http://hdl.handle.net/11858/00-001M-0000-0014-07E4-6 [located on Jul. 21, 2016].

* cited by examiner

*Primary Examiner* — Thane Underdahl
(74) *Attorney, Agent, or Firm* — Benoit & Côté Inc.

(57) ABSTRACT

The invention relates to methods and instruments for determining the resistances of microbes to antibiotics, in particular those microbes which produce beta-lactamases. The method determines the resistance of the microbes in less than an hour by incubating a tiny quantity of the microbes on a mass spectrometric sample support plate after they have been combined with a dosed quantity of a suitable antibiotic, for example the beta-lactam antibiotic imipenem, and by direct mass spectrometric measurement of the breakdown of the antibiotic by the microbial enzymes.

14 Claims, 2 Drawing Sheets

RAPID TEST FOR MICROBIAL RESISTANCES BY MASS SPECTROMETRY

BACKGROUND OF THE INVENTION

Field of the Invention

The invention relates to the determination of microbial resistance to antibiotics, in particular those microbes which produce beta-lactamases.

Description of the Related Art

The publication WO 2011154517 A1 (M. Kostrzewa, K. Michelmann, K. Sparbier) and the equivalent publications DE 102010023452 B4 and US 20130095511 A1 present a method to determine microbial beta-lactamase resistances which is based on the mass spectrometric measurement of the enzymatic modification of beta-lactam antibiotics, or substrates with a similar structure, by microbial beta-lactamases. To this end, bacteria are introduced into solutions with beta-lactam antibiotics, or substrates with a similar structure, and incubated for around three hours, for example. The bacteria are then preferably separated out by centrifugation or filtration. One to two microliters of the solution containing no bacteria is subsequently applied to a mass spectrometric sample support, dried, and coated with a matrix solution for ionization by matrix-assisted laser desorption (MALDI). Measurement in a time-of-flight mass spectrometer with a MALDI ion source produces a mass spectrum from which it is possible to determine whether an enzymatically modified antibiotic or substrate is present, especially a hydrolytic splitting of the beta-lactam ring, which indicates that the microbes are resistant.

A similar method is presented in the publication WO 2012/023845 A1 (Luider et al.), where in general the modifications of antibiotics by microbial enzymes are determined by mass spectrometry.

The methods described in these documents have a relatively large number of individual steps, especially centrifugation or filtration, which takes a lot of time and often involves manual procedures. The known methods normally take around three hours. There continues to be a need for methods to determine microbial resistances which involve less work, are easier to automate and faster, and allow a high sample throughput with smaller sample quantities.

There is an ongoing need to provide methods and instruments for determining a microbial resistance, which is based on an enzymatic modification of antibiotics, by mass spectrometry wherein the methods comprise only a few individual steps and preferably last less than an hour.

SUMMARY OF THE INVENTION

The invention provides a method for determining the resistance of a microbial sample to an antibiotic, wherein the microbial sample and the antibiotic are brought together in a volume of liquid on a test site of a sample support, and a mass spectrometric measurement at the test site analyzes whether the antibiotic is enzymatically modified. The mass range of the mass spectrometric measurement is preferably smaller than 1000 daltons, in particular between 250 and 750 daltons.

The antibiotic can be a beta-lactam antibiotic from the group of penicillins (benzylpenicillins, oral penicillins, aminopenicillins, isoxacylpenicillins, acylaminopenicillins), the cephalosporins, the monobactams or the carbapenems. The microbial sample can also be brought together with a combination drug product consisting of a beta-lactam antibiotic and a beta-lactamase inhibitor, e.g. clavulanic acid in combination with amoxicillin, tazobactam in combination with piperacillin, or sulbactam with a beta-lactam antibiotic. The microbial sample can also be combined with more than one antibiotic at the test site.

An enzymatic modification of the antibiotic is, for example, determined by a decrease in the antibiotic, or an increase in one or more breakdown products, or both, as revealed by the corresponding mass signals. The decrease in the antibiotic can be determined in particular by means of a comparison with the mass signal of a reference substance. The test site in this case can already be coated with the reference substance before the microbial sample and the antibiotic are combined. It is also possible to add the reference substance after they have been combined or during the preparation of a sample suitable for mass spectrometric measurement, e.g. a MALDI sample.

In a preferred embodiment, the mass spectrometric measurement is conducted in a mass spectrometer with a MALDI ion source, in particular in a time-of-flight mass spectrometer, where the mass spectrometric sample support is flat and has a multiplicity of test sites.

In a further embodiment, the microbial sample preferably has intact microbial cells. In the method according to the invention, the incubation period of the microbial cells in the volume of liquid is less than an hour, for example, preferably only around half an hour. The incubation in the volume of liquid is preferably conducted at room temperature. The number of microbial cells applied onto a test site preferably amounts to between $10^3$ and $10^7$. When intact microbial cells are used, it can be advantageous that the microbial cells also remain intact, i.e. are not digested (lysed), during preparation of the sample used for the mass spectrometric measurement, especially during preparation of a MALDI sample.

The microbial sample can consist of intact microbial cells taken from a colony of a flat nutrient medium (e.g. an agar plate) or separated from a liquid nutrient medium by centrifugation or filtration. The liquid nutrient medium can, in particular, be a positive blood culture, where the blood cells are preferably destroyed before the centrifugation or filtration. The microbial sample can also be a non-incubated sample of a body fluid, such as a blood sample, a urine sample, or a sample of a spinal fluid, or a smear sample. A smear sample is endogenous material for analysis from the surface of wounds or mucous membranes (mouth, nose, urethra, vagina, anus).

In a different embodiment, the microbial sample consists of digested microbial cells (cell lysate), in which case the digestion of the microbes can also be conducted at the test site. If intact microbial cells of the microbial sample are digested by preparing a MALDI sample at the test site, or if the microbial sample is a cell lysate, mass signals of microbial proteins can also be acquired in the mass spectrometric measurement. These signals can be additionally used to identify the microbes taxonomically and/or to characterize them further in respect of their resistance behavior. A microbial sample can also be obtained by sampling microbial cells of a colony on a flat nutrient medium using a liquid not containing any antibiotic and then combining the sample liquid, as a microbial sample, with the antibiotic on the sample support.

In a further embodiment, the volume of liquid at the test site is less than ten microliters, preferably less than five microliters, and in particular between one and three microliters. After the microbial sample and the antibiotic have been combined on a test site of a sample support, the sample support is preferably kept in a humid environment, or additional liquid is added to the test site in order to prevent the volume of liquid from drying up for a specified incubation period or reaction time.

The invention furthermore provides a sample support for a mass spectrometric determination of the resistance of a microbial sample, wherein the sample support has a multiplicity of test sites and at least one test site is coated with a dosed quantity of one or more antibiotics. Different test sites can be coated with different antibiotics. Moreover, each test site can be additionally coated with one or more reference substances.

In principle, the mass-spectrometric measurement can be carried out with any mass spectrometer, such as a quadrupole filter (in particular a triple-quadrupole mass spectrometer), a time-of-flight mass spectrometer with orthogonal ion injection (OTOF), an ion cyclotron resonance mass spectrometer (ICR-MS), an electrostatic Kingdon mass spectrometer or an ion trap mass spectrometer. It is particularly favorable to use the same MALDI time-of-flight mass spectrometer which is currently routinely used for the identification of microbes, in particular bacteria, and which is usually operated in linear mode without a reflector.

The invention has the advantages of using only small quantities of microbes and small volumes of liquids, of needing only a few simple individual steps, and in particular of being very rapid. The method according to the invention allows, in particular, a mass spectrometric determination of resistance without the need to separate microbial cells from a volume of liquid by centrifugation or filtration.

BRIEF DESCRIPTION OF THE DRAWINGS

The top MALDI mass spectrum in FIG. 1 depicts the mass signals of imipenem which has not been broken down (identified by arrows) after incubation with a beta-lactamase-negative strain. The bottom MALDI mass spectrum shows that the mass signals of the imipenem have disappeared after half an hour of incubation with a beta-lactamase-positive strain on a sample support. The vertical line shows the position of the reference substance.

DETAILED DESCRIPTION

Figure 1:
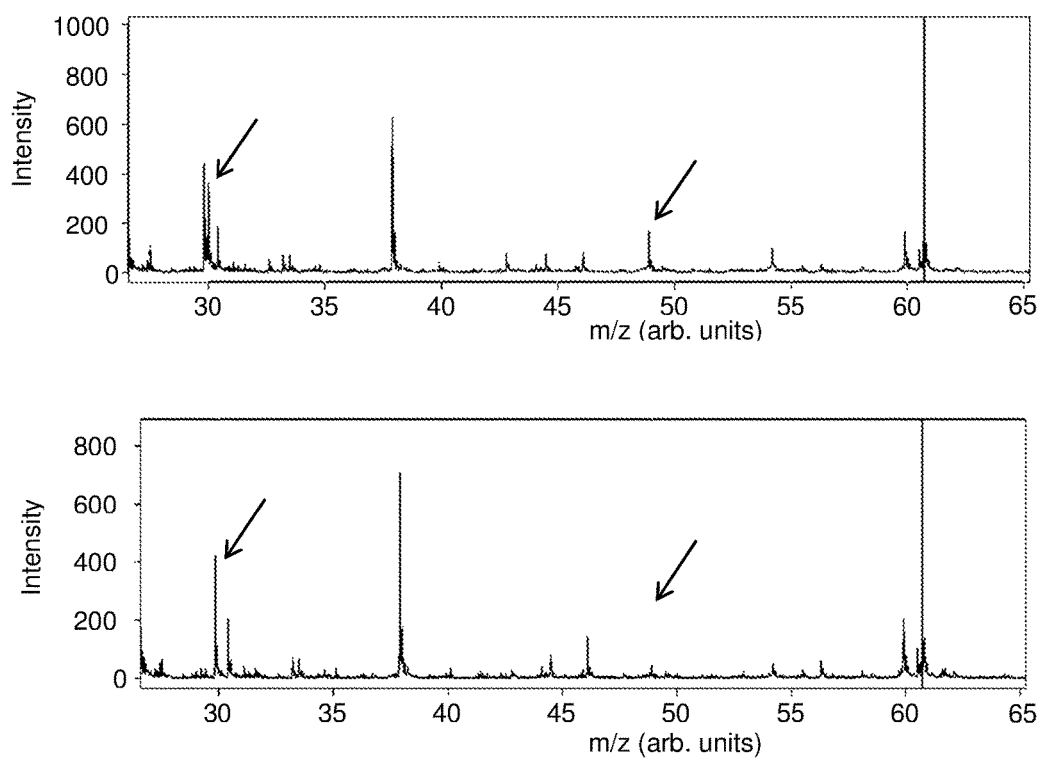

Many species of microbe, particularly bacteria, archaea and unicellular fungi, can be quickly and easily identified mass spectrometrically by taking small quantities of microbes from a colony cultured in the usual way on or in a nutrient medium and transferring them onto a mass spectrometric sample support plate, where they are digested with a solution of a matrix substance, dried, and measured mass—spectrometrically by ionization by matrix-assisted laser desorption. The profile, containing around 40 to 80 proteins in each case, which are typically in the mass range between 3000 and 20000 daltons, is used to determine the identity of the microbes by similarity analyses with thousands of reference spectra. The term "identification" here is deemed to mean the taxonomic classification, i.e. the determination of family, genus, species and possibly subspecies. There are meanwhile libraries with reference spectra of thousands of microbial species which are medically and legally admissible, including practically all clinically relevant species.

In the medical field, however, there is not only the problem of a fast identification, but also the problem of detecting resistances to the commonly used antibiotics. Rapid prevention and control of infection is often not possible without knowledge of the resistances. It is therefore necessary to have not only methods for fast identification of microorganisms, but also methods for quickly determining and characterizing their resistances.

Since the first use of penicillin, a beta-lactam antibiotic, bacteria have increasingly developed different types of resistances. One type of bacterial resistance to beta-lactams consists in the formation of enzymes (beta-lactamases) which catalytically break open the beta-lactam ring by hydrolysis and thus render it ineffective. The catalytic effect of these enzymes means that a small amount of beta-lactamases is sufficient to destroy large quantities of beta-lactam antibiotics. Several hundred variants of beta-lactamases, which are formed by different types of bacteria, are currently known. The genetic information for the synthesis of the enzyme, which is initially produced by mutations, is inherited chromosomally or plasmidally. The plasmidal information can also be transferred between bacteria, even between bacteria of different species ("horizontal transfer"), by various mechanisms, thus making it possible for resistant bacteria to spread rapidly.

Today there are a large number of derivatives of beta-lactam antibiotics, among them several penicillins (benzylpenicillins, oral penicillins, aminopenicillins, isoxazolyl penicillins, acylaminopenicillins), as well as cephalosporins, monobactams and carbapenems, listed here by breadth of effectivity in ascending order. The most effective beta-lactam antibiotics are usually derivatized with larger chemical groups in order to sterically hinder the beta-lactamases. On the other hand, new and more effective beta-lactamases are constantly forming through mutations in bacteria. The feared "extended spectrum beta-lactamases" (ESBL) and the "carbapenemases" can split a large spectrum of beta-lactam antibiotics. The ESBL were first formed by spot mutations on a beta-lactamase. The genes for the ESBL and for the carbapenemases are to be found on plasmids, which can be transferred horizontally from bacterium to bacterium.

ESBL-carrying bacteria are resistant to penicillins, cephalosporins (generations 1-4) and to monobactams. It is mainly *E. coli* and *Klebsiella* (Gram-negative bacteria) which carry ESBL genes. Microbiologists are watching the rapid spread of these ESBL resistances and of the carbapenem resistances, too, with a great deal of concern. It is one of the most worrying issues in infection research, alongside the methicillin resistance of *Staphylococcus aureus* (MRSA), cf. for example "Rapid Spread of Carbapenem-Resistant Klebsiella pneumoniae in New York City, a New Threat to Our Antibiotic Armamentarium", S. Bratu et al., Arch Intern Med 2005, 165(12), 1430-1435.

Beta-lactamase inhibitors are one tool against beta-lactamases. They are administered together with beta-lactames in order to weaken the effect of beta-lactamases present in the bacterium. Established combination drugs are clavulanic acid+amoxicillin, sulbactam+ampicillin, tazobactam+piperacillin, for example. Not all combinations have the optimum effect. These treatments should, however, only be used after careful identification of the bacteria and careful determination of their resistance because it is to be expected that this tool will also very quickly become blunt.

The invention provides a method which requires only small quantities of bacteria and which allows a microbial resistance to be measured particularly easily and quickly on the basis of a catalytic effect of microbial enzymes on antibiotics. Microbial beta-lactamases cause a hydrolytic splitting of the beta-lactam ring of corresponding antibiotics, for example. The method can determine the resistance of the microbes in less than an hour. It is preferable to combine a small quantity of intact microbial cells with a dosed quantity of an antibiotic on a mass spectrometric sample support plate and to incubate them there. The breakdown of the antibiotic caused by the catalytic effect of the microbial enzymes is measured with the aid of mass spectrometry. Surprisingly, the incubation period can be less than an hour, and usually around half an hour. It is preferable to carry out the incubation at only room temperature and in a humid environment in order to prevent the sample drying up.

Figure 3:
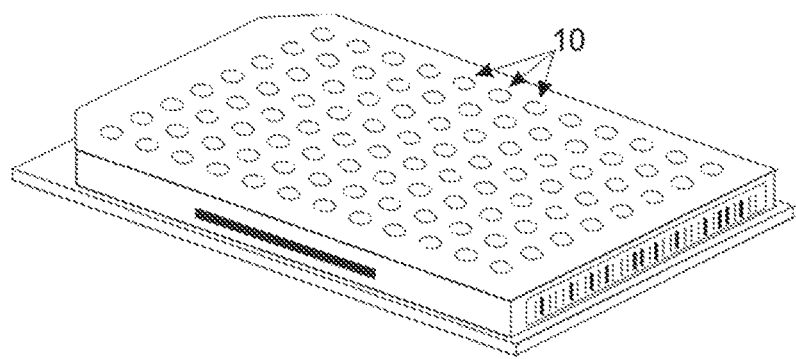
FIG. 3 shows, by way of example, a sample support plate the size of a microtitration plate with 96 test sites (10), which are coated with doses of antibiotics. Different, usually smaller, sample support plates exist for other types of mass spectrometers. Particularly advantageous are sample support plates whose test sites (10) have a hydrophilic surface embedded in a hydrophobic environment. Any liquids applied then flow of their own accord up to the edge of the test sites.

In addition, the invention includes mass spectrometric sample supports (sample support plate) and methods for their fabrication. A sample support plate according to the invention is shown in FIG. 3. It is preferably flat and has several test sites (10), each of which is already prepared with at least one layer of a dosed antibiotic. The sample support plate can contain test sites with layers of different antibiotics, which can be used to simultaneously test a microbial sample for different resistances. It is also possible to have test sites with layers of antibiotics with inhibitors for the reactions of the microbial enzymes. The layers can also contain dosed quantities of reference substances, which can be used both for a re-calibration of the mass scale, and for determining quantitative changes in the mass signals of the antibiotic(s), including their breakdown products.

In the method according to the invention, the resistance of the microbes is preferably determined by combining and briefly incubating a small quantity of the microbes with a fixed quantity of a suitable antibiotic directly on a mass spectrometric sample support plate. The surprising aspect here is that the breakdown of the antibiotic by the microbial enzymes can be detected after just a half-hour incubation period at room temperature and subsequent drying and preparation of a MALDI sample, if the MALDI sample is directly measured in a mass spectrometer with a MALDI ion source, without removing the microbes from the sample support.

A most preferable method, split up in detail into individual method steps, is described as follows:
a) Provision of a sample support plate which has a layer containing a dosed quantity of an antibiotic on at least one test site,
b) Application of the microbes onto the layer of antibiotic and application of a liquid onto this test site,
c) Incubation on the test site, particularly in a humid environment at room temperature,
d) Drying,
e) Preparation of a sample for matrix-assisted laser desorption and ionization (MALDI),
f) Measurement of the mass spectrum in a mass spectrometer with a MALDI ion source, in particular with a time-of-flight mass spectrometer, and
g) Evaluation of the mass spectrum to identify the resistance.

The layer on the test site contains, for example, around 0.1 to 2 micrograms, preferably 0.5 micrograms, of antibiotic. It can additionally contain a known quantity of a reference substance. Similar to a taxonomic identification, only around $10^3$ to $10^7$ microbes are smeared onto each test site. One to three, preferably around two, microliters of liquid, are applied onto each test site for the incubation. Different test sites of the same sample support plate can contain layers with different antibiotics. The layers may contain not only an antibiotic, but also an additional inhibitor to reduce the effectiveness of the microbial enzyme.

The microbial cells can be smeared on manually or with automated application, by means of an inoculating system, for example. A method for the mass spectrometric analysis of microbes on the surface of a nutrient medium is disclosed in document DE 102012011647 A1, where the microbial cells are transferred by direct contact from the surface of a flat nutrient medium onto a contact surface of a sample support. The sample support here can be flat, with a large surface area, or it can be a pin-shaped sample support whose end surface is brought into contact with the microbial cells of a colony. The contact surface of the pin-shaped sample support is so small that only microbes of a single colony are transferred onto the pin-shaped sample support. After the microbial cells have been transferred, the pin-shaped sample support can be inserted into an adapter plate in such a way that the end surface of the pin-shaped sample support essentially fits flush with the surface of the adapter plate. In the present invention, the end of a pin-shaped sample support can be coated with one or more antibiotics.

The method according to the invention is explained hereinafter using an example for the broad-spectrum imipenem, a carbapenem.

A mass spectrometric MALDI sample support plate usually has a large number (48-386) of clearly marked test sites with diameters of two to four millimeters. Particularly favorable are hydrophilic test sites in hydrophobic surroundings. FIG. 3 shows such a sample support plate with 96 test sites (10) by way of example; here it is the size of a microtitration plate, but smaller versions of sample support plates are also available. To produce a sample support plate according to the invention, at least some test sites of a sample support plate can each be coated with two microliters of an imipenem solution (or a corresponding antibiotic) and dried so that the sample support contains 0.5 micrograms of imipenem per test site in each case. After drying, the sample support plate is stored with protection against humidity, for example shrink-wrapped and provided with a desiccant. Sample support plates with these preparations can be made commercially available so that there is no need for this preparation step in the laboratory.

Bacteria which have grown as colonies on an agar plate are smeared manually onto the dry imipenem layers using a suitable tool, for example a hygienically clean toothpick, in the same way as a smear preparation for the microbe identification. This can be carried out in the same step and with the same toothpick used to produce a sample for the microbe identification. The test site for the identification has no antibiotic. When all the bacteria under investigation have been applied to the test sites of the sample support, two microliters of a ten millimolar ammonium bicarbonate buffer (pH 8) is pipetted onto each one, whereby imipenem and bacteria mix with each other, and the bacterial cells are mostly not digested. The sample support is subsequently incubated for thirty minutes at room temperature in a box which is kept humid in order to prevent the sample on the test site from drying up prematurely. After the incubation phase, the samples are dried on the sample support and then coated with matrix solution containing only very little trifluoroacetic acid so that the bacterial cells are not digested. The matrix used was α-cyano-4-hydroxycinnamic acid (HCCA) in a concentration of 10 milligrams per milliliter in a mixture of water, 50% acetonitrile and 0.2% trifluoroacetic acid. After drying again, a mass spectrum is acquired from this preparation in a MALDI time-of-flight mass spectrometer in the usual way.

It is usual to form the differentiation value $LogRQ_H$ to evaluate the mass spectra:

$$LogRQ_H = Log\frac{\Sigma\,\text{internal reference}}{\Sigma\,\text{intensities not hydrolyzed}},$$

which usually results in values above zero for beta-lactamase-positive microbes, and values below zero for beta-lactamase-negative microbes.

The top part of FIG. 1 shows a measured MALDI mass spectrum obtained from microbes which are susceptible to imipenem, using the method and sample supports according to the invention. The arrows here indicate mass signals of imipenem which has not been broken down. The bottom part of FIG. 1 depicts a measured MALDI mass spectrum of resistant microbes, whose enzymes have quantitatively hydrolyzed the imipenem in only half an hour so that the mass signals of the imipenem indicated by arrows have disappeared. The enzymatic splitting reactions are quite rapid: provided they are not hindered by the gradual shortage of substrates, they take roughly between one and a hundred milliseconds per molecular reaction, with characteristic differences for the different beta-lactamases.

The present example with imipenem is unusual in that the enzymatically hydrolyzed imipenems have no mass signals in the MALDI mass spectrum, which makes it necessary to measure the breakdown of the imipenem molecules in this case. An internal reference substance is required for this, which expediently is already added to the imipenem preparation on the sample support plate. Thiamine can be used as the internal reference substance, for example. The vertical line in the two mass spectra shown in FIG. 1 indicates the position of the reference substance. It should be noted here that it is also possible to add the reference substance later, for example in the matrix solution.

When evaluating the mass spectra, the mass signal of the internal reference substance can be used, on the one hand, to recalibrate the mass axis of the mass spectra; on the other hand, with imipenem especially, it is also used to calculate the breakdown rate (hydrolysis rate). As explained above, imipenem is a special case insofar as the hydrolysis products cannot be detected in the MALDI mass spectrum, even though they are present (with other types of ionization, such as electrospray ionization (ESI), the hydrolysis products can be measured). In order to at least detect the reduction of the non-hydrolyzed imipenem peaks, the internal reference substance is used to calculate the hydrolysis rate:

$$LogRQ_{RI} = Log\frac{\Sigma\,\text{internal reference}}{\Sigma\,\text{intensities not hydrolyzed}}.$$

Figure 2:
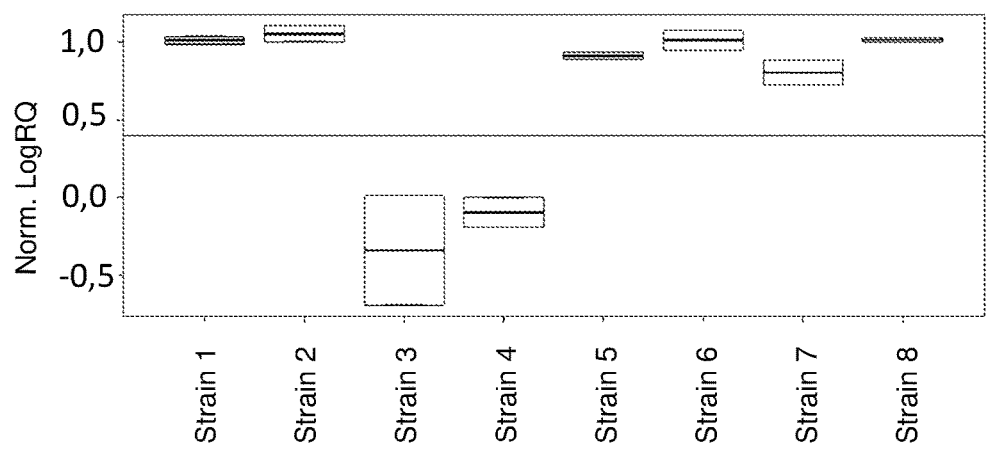
FIG. 2 is a "boxplot diagram" which shows the quotients logRQ of six beta-lactamase-positive strains, each with logRQ>0.4, and two beta-lactamase-negative strains, each with logRQ<0.2. Medians and spreads from several measurements are shown.

After normalization of the hydrolysis rate to a suitable negative and positive control, a normalized hydrolysis rate of norm·logRQ>0.4 indicates resistant microbes, while values of norm·logRQ<0.2 are measured for susceptible microbes. FIG. 2 shows the results for two susceptible and six resistant microbes, measured with an imipenem coating on a sample support plate according to the aforementioned fabrication method.

In principle, the mass spectrometric measurement in the method according to the invention can be carried out with any mass spectrometer, but it is particularly favorable to use the same MALDI time-of-flight mass spectrometer which is currently routinely used for the identification of microbes, especially bacteria, and which is usually operated in linear mode. The mass spectra shown in FIG. 1 were acquired with a MALDI time-of-flight mass spectrometer in linear mode.

Usually, the microbes of a sample under analysis are initially cultured on an agar nutrient medium until they form colonies in order to then be applied to a test site of the sample support with a tool, both for identification and also to determine resistances. For the identification, care is usually taken that only microbes of a single colony are sampled. To determine the resistances, however, it is often advantageous to mix the microbes of several colonies, at least five or so, in order to also obtain useful results for mixed resistances.

Another important type of culture is the blood culture, which is used for diagnosed or suspected sepsis. The patient is usually treated immediately with the very broad-spectrum imipenem, since sepses are extremely dangerous and have a high mortality rate. After a few hours of cultivation, the blood cells are destroyed by suitable means and the microbes of the sepsis can be precipitated by careful centrifugation or filtration so as not to damage the microbes. Some of the microbial cells can be used for a taxonomic identification, the others for testing resistance to imipenem according to the invention. If such a resistance to imipenem is present, it is possible to continue the treatment with combination drugs, which can be selected more specifically because the microbe species is known through the simultaneous identification.

In general, it is not only the resistance to a single antibiotic which is of interest. The method according to the invention also makes it possible to develop multiple-resistance tests with the introduction of several different types of antibiotics, which can be deposited onto different test sites of one sample support plate, but also onto one single test site. It is possible to produce sample support plates which already contain series of different antibiotics, with reference substances if required. It is also possible to apply antibiotics together with inhibitors (combination drugs) in additional test sites. In the resistance test with different antibiotics at different test sites, the same tool can be used to distribute the microbes being tested over the various test sites. The pipetting of the buffer, the incubation, preparation and mass spectrometric measurement are conducted as explained in the example above. The evaluation can be done using a program which also controls the measurement in the mass spectrometer and knows the slightly different parameters for the evaluation of the mass spectra of the different test sites. The resistance to various antibiotics is thus measured in one run, which takes only slightly longer than determining the resistance to one antibiotic.

There are also cases of mixed samples where the interest focuses less on identification and more on an immediate resistance determination. It is extremely important, for example, to know whether resistant germs are present in a swab of the nasal mucosa or in the nasal secretion. The usual procedure is to use a swab of the nasal or oral mucosa to investigate whether a patient, on admission to a hospital, or a staff member of a hospital is a carrier of a microbial resistance. Such a swab or nasal secretion can be applied as a microbial sample directly onto appropriately pre-prepared test sites of a sample support, for which purpose a test site has preferably more than one antibiotic in view of the large number of these types of resistance determinations in a hospital. The situation is similar for other types of infection, for example in suppurating wounds.

The invention is not limited to the embodiments or examples stated here. The ionization can also be performed with the aid of DESI (Desorption Electrospray Ionization) from a flat sample support, for example, or also directly from the surface of a flat nutrient medium, which serves as the sample support and onto which a liquid containing the antibiotic is applied. In addition to ionization by MALDI, laser desorption from a flat sample support with subsequent chemical ionization, for example, is also possible.

The invention claimed is:

1. Sample support for a mass spectrometric determination of the resistance of a microbial sample to be applied to the sample support, wherein the sample support plate is flat and has on its surface a multiplicity of test sites and at least one test site is coated with a dosed quantity of one or more antibiotics and with one or more reference substances.

2. The sample support according to claim 1, wherein different test sites are coated with different antibiotics.

3. The sample support according to claim 1, wherein the dosed quantity is around 0.1 to 2 micrograms.

4. The sample support according to claim 1, wherein the one or more antibiotics is a beta-lactam antibiotic.

5. The sample support according to claim 4, wherein the beta-lactam antibiotic is from the groups of penicillins, the cephalosporins, the monobactams or the carbapenems.

6. The sample support according to claim 5, wherein the beta-lactam antibiotic is from the groups of benzylpenicillins, oral penicillins, aminopenicillins, isoxacylpenicillins, or acylaminopenicillins.

7. The sample support according to claim 4, wherein the one or more antibiotics is a beta-lactam antibiotic in combination with a beta-lactamase inhibitor.

8. The sample support according to claim 7, wherein the beta-lactamase inhibitor is sulbactam.

9. The sample support according to claim 7, wherein the one or more antibiotics is amoxicillin in combination with clavulanic acid, piperacillin in combination with tazobactam or ampicillin in combination with sulbactam.

10. The sample support according to claim 1, wherein said mass spectrometric determination is a mass spectrometric determination using matrix assisted laser desorption/ionization (MALDI).

11. The sample support according to claim 1, wherein the tests sites have a capacity of less than 10 microliters.

12. The sample support according to claim 11, wherein the tests sites have a capacity between one and three microliters.

13. The sample support according to claim 1, wherein the number of test sites is between 48 and 386.

14. The sample support according to claim 1, wherein the test sites are hydrophilic with hydrophobic surroundings.

* * * * *